(12) United States Patent  
Russo et al.

(10) Patent No.: US 7,405,296 B2  
(45) Date of Patent: Jul. 29, 2008

(54) ADDITIVES FOR FLUORINATED OILS

(75) Inventors: Antonio Russo, Milan (IT); Patrizia Maccone, Milan (IT)

(73) Assignee: Solvay Solexis S.p.A., Milan (IT)

( * ) Notice: Subject to any disclaimer, the term of this patent is extended or adjusted under 35 U.S.C. 154(b) by 100 days.

(21) Appl. No.: 11/402,930

(22) Filed: Apr. 13, 2006

(65) Prior Publication Data  
US 2007/0032390 A1 Feb. 8, 2007

(30) Foreign Application Priority Data  
Apr. 14, 2005 (IT) .......................... MU2005A0646

(51) Int. Cl.  
*C07D 251/30* (2006.01)  
*C07D 251/38* (2006.01)  
*C07D 251/42* (2006.01)  
*C07D 251/48* (2006.01)  
*C10M 169/04* (2006.01)

(52) U.S. Cl. .................. 544/180; 544/215; 508/257; 508/182; 252/400.23

(58) Field of Classification Search ................ 544/180, 544/215; 528/362; 508/257  
See application file for complete search history.

(56) References Cited

U.S. PATENT DOCUMENTS 3,214,478 A 10/1965 Milian, Jr. et al.  
3,242,218 A 3/1966 Miller et al.

(Continued)

FOREIGN PATENT DOCUMENTS

| EP | 0 148 482 A2 | 7/1985 |
| EP | 0 597 369 B1 | 5/1994 |
| EP | 1 354 932 A1 | 10/2003 |
| EP | 1 454 938 A1 | 9/2004 |
| GB | 1 104 432 | 9/1968 |
| GB | 1 226 566 | 3/1971 |
| WO | WO 99/51612 | 10/1999 |

OTHER PUBLICATIONS

Snyder et al.; "Development of Polyperfluoroalkylethers as High Temperature Lubricants and Hydraulic Fluids"; ASLE Transactions, 13(3), pp. 171-180; 1975.

*Primary Examiner*—Venkataraman Balasubram  
(74) *Attorney, Agent, or Firm*—Arent Fox LLP

(57) ABSTRACT

Compounds of formula

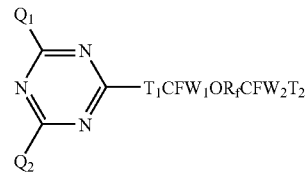

(I)

wherein  
$R_f$ is a (per)fluoropolyoxyalkylene chain having a number average molecular weight in the range 500-10,000;  
$W_1$, $W_2$, equal to or different from each other, are —F or —$CF_3$;  
$T_1$ is equal to —$CHA_a$—$B_a$ ($CH_2CH_2O)_{na}$— wherein $A_a$=H, $CF_3$; $B_a$=O, S, NH; na=0 or an integer between 1 and 6;  
$T_2$ is equal to —F, —$CF_3$, —$C_2F_5$, —$(C_2F_4)$ Cl, or a group of formula:

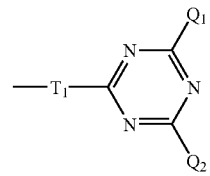

$Q_1$, $Q_2$ equal to or different from each other, are a chain of formula -$T_{1-l\ -CFW_1}$—O—$R_f$—$CFW_2$-$T'_2$, wherein: $T'_2$ is equal to —F, —$CF_3$, —$C_2F_5$, —$(C_2F_4)$ Cl; or is a group of formula:

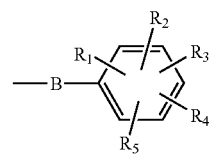

wherein B is equal to O, S, NH; R1, R2, R3, R4, R5 equal to or different from each other are selected from H, F, $NO_2$, CN, $C_1$-$C_8$ perfluoroalkyl, carboxyl, phenyl (Ph), O- Ph, NH-Ph, S-Ph;  
wherein B is equal to O, S, NH; R1, R2, R3, R4, R5 equal to or different from each other are selected from H, F, $NO_2$, CN, $C_1$-$C_8$ perfluoroalkyl, carboxyl, phenyl (Ph), O- Ph, NH-Ph, S-Ph;  
with the proviso that at least one of $Q_1$ and $Q_2$a is equal to:

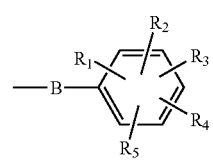

20 Claims, No Drawings

U.S. PATENT DOCUMENTS

| | | |
|---|---|---|
| 3,665,041 A | 5/1972 | Sianesi et al. |
| 3,715,378 A | 2/1973 | Sianesi et al. |
| 4,523,039 A | 6/1985 | Lagow et al. |
| 4,681,693 A | 7/1987 | Gavezotti et al. |
| 5,124,058 A | 6/1992 | Corti et al. |
| 5,326,910 A | 7/1994 | Paciorek et al. |
| 5,550,277 A | 8/1996 | Paciorek et al. |
| 5,942,598 A | 8/1999 | Iwa et al. |
| 6,156,937 A | 12/2000 | Marchionni et al. |
| 6,509,509 B2 | 1/2003 | Tonelli et al. |

ADDITIVES FOR FLUORINATED OILS

The present invention relates to additives for lubricating oils and greases capable to improve their thermal stability in the presence of metals and in oxidative environment (for example air) and their preparation process.

Particularly the invention relates to additives having a perfluoropolyether structure capable to stabilize lubricants, such as oils and greases, preferably having a perfluoropolyether structure, in combination with to the capability of conferring good anti-rust properties and good stability (high shelf life) to storage at 25° C., i.e. without phase separation.

It is known in the prior art that perfluoropolyethers have a good chemical and thermal stability, and are used as lubricating oils and greases, or as hydraulic fluids in applications where a broad thermal rating is required, and in particular severe conditions, for example in contact with corrosive compounds or with ionizing radiations. However these lubricants show the drawback that in some extremely drastic operating conditions, as for example at temperatures higher than 280° C., in oxidative environment (for example air) and in the presence of metals, tend to decompose showing a limited thermal stability.

The decomposition process in the above described conditions brings to the fragmentation of the perfluoropolyether chains or, in some cases, to the total decomposition of the lubricant itself, thus compromising the lubricant performances.

Furthermore the fluid decomposition is generally associated with a progressive corrosion of the metal itself.

It is also known in the prior art that the resistance to oxidation of oils and greases having a pefluoropolyether structure, at high temperatures in the presence of metals, can be improved with the use of specific stabilizing additives. They must have as peculiarity a good compatibility with the perfluoropolyether oil. Stabilizing additives containing phosphor and fluorinated substituents are known.

U.S. Pat. No. 4,681,693 describes stabilizers for perfluoropolyether lubricants having a backbone formed of arylphosphines units, or their derivatives, linked to perfluoropolyether chains through oxygen or sulphur atoms. These compounds are prepared with a multistep process comprising intermediates difficult to be prepared. Therefore this process is hardly industrially usable.

EP 597,369 describes stabilizers for phosphazene derivatives based perfluoropolyether lubricants, having contemporaneously on the phosphazene ring both aromatic groups and (per)fluoropolyether chains. The synthesis of the stabilizers is not selective and does not allow to obtain an additive having a well defined chemical structure. Besides the phosphazene precursor is very expensive and therefore disadvantageous from an industrial point ov view. Tests carried out by Applicant have shown that these compounds have a low stability to storage.

U.S. Pat. No. 5,326,910 describes perfluoropolyether phosphotriazines as stabilizers for perfluoropolyether oils. These derivatives are obtained by a synthesis requiring many steps and reactants difficult to prepare, as perfluorinated epoxides.

In U.S. Pat. No. 5,550,277 stabilizers for perfluoropolyether lubricants having the structure of aromatic phosphates or phosphonates substituted by perfluoropolyether chains are described. The synthesis process is very complicated and requires many steps and the use of organometallic reactants, as for example butyl lithium, which, as well known, are difficult to use in industry for plant safety.

In the patent application WO 99/51,612 phosphoric esters, in particular arylphosphates, are described, wherein at least one of the substituents is a perfluoropolyether chain. In the preparation of said additives aromatic chloroesters are used. These compounds have the drawback to be very expensive. Besides, as described in the examples of this document, the phosphoric esters are obtained by reaction of aromatic alcohols with $POCl_3$, which is toxic and scalding, thus requiring specific equipments for the use on industrial scale.

The stabilizers containing phosphor described so far, although having good stabilizing properties, are however obtained with synthesis processes comprising various steps, some of them require the use of expensive and/or difficult to prepare reactants, requiring operating conditions or technological solutions of difficult management on industrial scale. Besides some of them show a poor stability to storage.

Not containing phosphor stabilizing additives for perfluoropolyether lubricants are also known.

For example in U.S. Pat. No. 5,942,598 oligomers having a perfluoroalkylenether-triazine structure are described, as lubricants having a good stability to the oxidation in the presence of metals. These oligomers can also be used as stabilizing additives for oils and greases having a perlfuoropolyether structure. However their synthesis requires various steps, some of them require the use of precursors of difficult preparation, with a yield in the final product lower than 40%, and therefore disadvantageous also from an economic point of view. Nothing is said on the anti-rust properties of said compounds.

In patent appliction EP 1,354,932 in the name of the Applicant, stabilizing additives having a perfluoropolyether structure not containing phosphor and having aryl end groups containing $NO_2$ groups are described. The additives are used to stabilize perfluoropolyether oils and greases in thermooxidative environment in the presence of metals. Tests carried out by the Applicant have shown that, even having good stabilizing performances, these additives show however the inconvenience of phase separation at room temperature. Therefore the compositions containing said additives have poor shelf life.

The need was therefore felt to have available additives:
capable to stabilize fluorinated lubricants, in particular having a perfluoropolyether structure, at high temperatures in oxidative environment and in the presence of metals;
showing anti-rust properties;
stable in fluorinated lubricating oils or greases at room temperatures without phase separation, thus obtaining compositions stable to storage (high shelf life);
obtainable by a simple industrial process.

The Applicant has surprisingly and unexpectedly found particular compounds having a perfluoropolyether structure capable to satisfy the above combination of properties.

An object of the present invention are compounds comprising perfluoropolyether chains and having at least one aryltriazine end group, of formula:

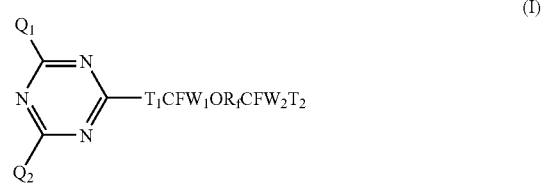

(I)

wherein
R$_f$ is a (per)fluoropolyoxyalkylene chain formed of one or more repeating units, statistically placed along the chain, having the following structure: (CFXO), (CF$_2$CF$_2$O), (CF$_2$CF$_2$CF$_2$O), (CF$_2$CF$_2$CF$_2$CF$_2$O), (CR$_6$R$_7$CF$_2$CF$_2$O), (CF(CF$_3$)CF$_2$O), (CF$_2$CF(CF$_3$)O), wherein X=F, CF$_3$; R$_6$ and R$_7$, equal to or different from each other, are selected from H, Cl, or perfluoroalkyl from 1 to 4 carbon atoms, said R$_f$ having a number average molecular weight in the range 500-10,000, preferably 500-5,000;

W$_1$, W$_2$, equal to or different frome ach other, are —F or —CF$_3$;

T$_1$ is equal to —CHA$_a$—B$_a$ (CH$_2$CH$_2$O)$_{na}$— wherein A$_a$=H, CF$_3$; B$_a$=O, S, NH; na is an integer from 0 to 6, extremes included;

T$_2$ is equal to —F, —CF$_3$, —C$_2$F$_5$, —(C$_2$F$_4$)Cl, or a group of formula:

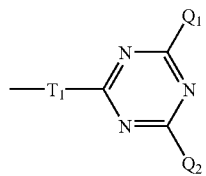

Q$_1$, Q$_2$, equal to or different from each other, are a perfluorooxyalkylene chain of formula:

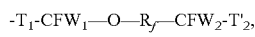

-T$_1$-CFW$_1$—O—R$_f$—CFW$_2$-T'$_2$, wherein T'$_2$ is equal to —F, —CF$_3$, —C$_2$F$_5$, —(C$_2$F$_4$)Cl; T$_1$, W$_1$ and W$_2$ have the above meaning;
or a group of formula:

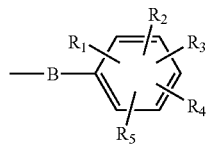

wherein B is equal to O, S, NH; R$_1$, R$_2$, R$_3$, R$_4$, R$_5$, equal to or different from each other, are selected from H, F, NO$_2$, CN, linear or branched C$_1$-C$_8$ perfluoroalkyl, carboxyl, phenyl (Ph), O-Ph, NH-Ph, S-Ph;

with the proviso that at least one of Q$_1$ and Q$_2$ is equal to the group:

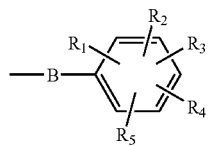

The preferred perfluoropolyether chain R$_f$ is selected from the following structures:

(A) —(CF$_2$CF(CF$_3$)O)$_a$(CFXO)$_b$— or
—(CF$_2$CF(CF$_3$)O)$_a$(CFXO)$_b$—CF$_2$(R'$_f$) CF$_2$—O—(CF$_2$CF(CF$_3$)O)$_a$(CFXO)$_b$— wherein R'$_f$ is a fluoroalkylene group from 1 to 4 C atoms; X is F or CF$_3$; a and b are integers such that the number average molecular weight is within the above range; a/b is between 10 and 100, b being different from 0;

(B) —(CF$_2$CF$_2$O)$_c$(CF$_2$O)$_d$(CF$_2$(CF$_2$)$_z$O)$_h$—
wherein c, d and h are integers such that the number average molecular weight is within the above range; c/d, d being different from 0, is between 0.1 and 10; h/(c+d), (c+d) being different from 0, is between 0 and 0.05; z is 2 or 3; h can also be equal to 0;

(C) —(CF$_2$CF(CF$_3$)O)$_e$(CF$_2$CF$_2$O)$_f$(CFXO)$_g$—
wherein X is F or CF$_3$; e, f, g are integers such that the number average molecular weight is in the above range; e/(f+g) is between 0.1 and 10, (f+g) being different from 0; f/g is between 2 and 10;

(D) —(CF$_2$ (CF$_2$)$_z$O)$_s$—
wherein s is an integer such as to give the above molecular weight, z has the already defined meaning;

(E) —(CR$_6$R$_7$CF$_2$CF$_2$O)$_{j'}$— or
—(CR$_6$R$_7$CF$_2$CF$_2$O)$_{p'}$—R'$_f$—O—(CR$_6$R$_7$CF$_2$CF$_2$O)$_{q'}$—
wherein R$_6$ and R$_7$ are equal to or different from each other and selected from H, Cl or perfluoroalkyl from 1 to 4 C atoms; R'$_f$ is a fluoroalkylene group from 1 to 4 C atoms; j', p' and q' are integers such as to have a molecular weight as the above mentioned one;

(F) —(CF(CF$_3$)CF$_2$O)$_{j''}$—
j'' being an integer such as to give the above molecular weight.

Preferably the R$_f$ structures in the compounds of formula (I) are selected between the structures (A) and (B).

The Applicant has surprisingly and unexpectedly found that the compounds of the invention can be used as additives of perfluorinated lubricants, as perfluoropolyether oils or perfluoropolyether base greases, to confer an improved thermal stability to the lubricant in oxidative environment and in the presence of metals in combination with good anti-rust properties and good shelf life at 25° C.

The pefluoropolyether compounds having at least one aryltriazine end group are transparent and odourless viscous liquids.

A further object of the present invention are lubricating compositions comprising:
from 99.95 to 90% by weight, preferably from 99.5 to 95%, of a perfluoropolyether oil or a PFPE based grease on perfluoropolyether oils;
from 0.05 to 10% by weight, preferably from 0.5 to 5% by weight, of at least one of the triazine compounds of formula (I).

Examples of perfluoropolyether oils are those belonging to the following classes:

(1) E-O—[CF$_2$CF(CF$_3$)O]$_{m'}$(CFXO)$_{n'}$-E'
wherein
X is equal to —F or —CF$_3$;
E and E', equal to or different from each other, are selected from —CF$_3$, —C$_2$F$_5$ or —C$_3$F$_7$;
m' and n' are integers such that the m'/n' ratio is between 20 and 1,000, n' being different from 0, and the viscosity of the product at 20° C. is between 10 and 4.000 cSt; the units being statistically distributed along the backbone.
These polymers can be obtained by perfluoropropene photooxidation, as described in GB 1,104,432, and by subsequent conversion of the end groups, as described in GB 1,226,566.

(2) C$_3$F$_7$O—[CF(CF$_3$)CF$_2$O]$_{o'}$-D
wherein
D is equal to —C$_2$F$_5$ or —C$_3$F$_7$;
o' is an integer such that the viscosity of the product is within the range indicated under (1).

These polymers can be prepared by ionic oligomerization of perfluoropropyleneoxide and subsequent-treatment with fluorine as described in U.S. Pat. No. 3,242,218.

(3) $\{C_3F_7O—[CF(CF_3)CF_2O]_{p'}—CF(CF_3)—\}_2$ wherein p' is an integer such that the viscosity of the product is within the range indicated under (1).

These products can be obtained by ionic telomerization of perfluoropropyleneoxide and subsequent photochemical dimerization as reported in U.S. Pat. No. 3,214,478.

(4) $E—O—[CF_2CF(CF_3)O]_{q'}(C_2F_4O)_{r'}(CFX)_{s'}-E'$ wherein

X is equal to —F or —$CF_3$;

E and E', equal to or different from each other, are selected from —$CF_3$, —$C_2F_5$ or —$C_3F_7$;

q', r' and s' are integers, including 0, so that the viscosity of the product is in the range indicated under (1).

These polymers can be obtained by photooxidation of a mixture of $C_3F_6$ and $C_2F_4$ and subsequent treatment with fluorine as described in U.S. Pat. No. 3,665,041.

(5) $E—O—(C_2F_4O)_{t'}(CF_2O)_{u'}-E'$ wherein

E and E', equal to or different from each other, are selected from —$CF_3$, —$C_2F_5$ or —$C_3F_7$;

t' and u' are integers such that the t'/u' ratio is between 0.1 and 5, u' being different from 0, and the viscosity of the product is in the reported range under (1).

These polymers are obtained by photooxidation of $C_2F_4$ as reported in U.S. Pat. No. 3,715,378 and subsequent treatment with fluorine as described in U.S. Pat. No. 3,665,041.

(6) $E—O—(CF_2CF_2CF_2O)_{v'}-E'$ wherein

E and E', equal to or different from each other, are selected from —$CF_3$, —$C_2F_5$ or —$C_3F_7$;

v' is a number such that the viscosity of the product is in the above reported range under (1).

These polymers are obtained as reported in EP 148,482.

(7) $D—O—(CF_2CF_2O)_{z'}-D'$ wherein

D and D', equal to or different from each other, are selected from —$C_2F_5$ or —$C_3F_7$;

z' is an integer such that the viscosity of the product is within the above reported range under (1).

These polymers can be obtained as reported in U.S. Pat. No. 4,523,039.

(8) $E_1-O(CF_2O)_n(CF_2CF_2O)_m—(CF_2CF_2CF_2O)_p(CF_2CF_2CF_2CF_2O)_q-E_2$ wherein $E_1$ and $E_2$ are perfluoroalkyl end groups equal to or different from each other, having formula —$(CF_2)_zCF_3$, wherein z is an integer from 0 to 3; n, m, p, q are integers such that the viscosity is as defined under (1), m/n is between 2 and 20, n being different from 0, preferably between 2 and 10;

the ratio (p+q)/(m+n+p+q) is between 0.05 and 0.2, (m+n+p+q) being different from 0; n/(m+n+q+p) ranges between 0.05 and 0.4, (m+n+p+q) being different from 0. These are obtained according to EP 1,454,938.

The preferred perfluoropolyether oils are those of the class (1), (4), (5) and (8).

The above mentioned perfluoropolyethers of the classes from (1) to (8) have perfluoroalkyl end groups, are liquid with a very low vapour pressure value and have a viscosity, at 20° C., generally between 10 and 100,000 cSt, preferably between 40 and 2,000 cSt.

The perfluoropolyethers usable for preparing oils and greases are available on the market as for example FOMBLIN® (Solvay Solexis).

The lubricant compositions of the present invention have a high shelf life at room temperature and do not visually show any substantially phase separation for long periods of time.

The compositions of the present invention can also contain other additives commonly used in perfluoropolyether lubricant formulations, as for example anti-wear additives.

A further object of the present invention is a process to obtain the triazine compounds of formula (I) comprising the following stages:

Stage A)

i) reaction of a perfluoropolyoxyalkylene derivative having formula $$T''_1-CFW_1—O—R_f—CFW_2-T''_2 \quad (II)$$

wherein $R_f$, $W_1$ and $W_2$ have the above meaning;

$T''_1$ and $T''_2$ can be equal to or different from each other, having general formula equal to —$CHA_a$—$B_a$($CH_2CH_2O)_{na}$—H, wherein $A_a$=H, $CF_3$; $B_a$=O, S, NH; na is an integer from 0 to 6, extremes included; or selected from F, $CF_3$, $C_2F_5$, $(C_2F_4)Cl$, with the proviso that at least one of the two end groups $T''_1$ and $T''_2$ is equal to —$CHA_a$—$B_a(CH_2CH_2O)_{na}$—H, preferably is selected from O—$CH_2OH$, O—$CH_2SH$, O—$CH_2NH_2$, $CH(OH)CF_3$;

with a trihalo-triazine of formula:

wherein J=Cl, F, preferably Cl;

at a temperature between 0° and 10° C., wherein the ratio between the equivalents of the compound (II) and the moles of (III) is equal to 1:1, in the presence of a solvent inert under the reaction conditions, capable to solubilize the reactants, and in the presence of an organic or inorganic base, preferably maintaining the reaction mixture under stirring;

ii) reaction of the product obtained in i) with an equivalent of a derivative of formula:

$$Q-H \quad (IV)$$

wherein Q has the above reported meaning for $Q_1$ and $Q_2$;

at a temperature in the range 25°-35° C.;

iii) reaction of the product obtained in ii) with an equivalent of a compound of formula (IV), equal to or different from the one used in step ii), at a temperature in the range 65° C.-100° C., preferably 70° C.-90° C.;

Stage B)

separation of the organic phase of the reaction mixture obtained in A) from the aqueous phase and subsequent separation, preferably by filtration, of the organic phase to remove the residual organic or inorganic insoluble salts;

Stage C)

several washings of the liquid organic phase with acid water and subsequent separation of the obtained compound of formula (I) from the organic solvent, for example by evaporation.

In stage A) the inert solvent is preferably selected from toluene, xylene, hexafluoroxylene, acetone, diethylketone, etc. The used solvent amount is depending on the reactant solubility in the solvent itself. In stage A) as inorganic base, NaOH, KOH, $Na_2CO_3$, $K_2CO_3$ can be used; as organic base, 2,6-dimethylpyridine, 2-methylquinoline, 2,4,6-trimethylpyridine(collidine) can be used. Preferably as base 2,4,6-trimethylpyridine is used.

The ratio between the equivalents of the base and the sum of the equivalents of compounds (II) and (IV) used in the above mentioned three steps of stage (A) is in the range 1:1-2:1, preferably 1:1-1.5:1.

The reaction times for each step are between 2 and 8 hours, preferably between 4 and 6 hours.

The compounds of formula (II) are known in the prior art, for example from U.S. Pat. No. 6,509,509 and U.S. Pat. No. 5,124,058.

The reactants having the structure (III), (IV) are known and commercially available.

The process of the present invention results particularly advantageous as the selective substitution of only one halogen atom of the triazine ring (III) which takes place in each step i), ii), iii) of stage A) allows the highly selective substitution of the halogen atoms of the triazine reactant (III) obtaining additives having a predetermined chemical structure.

Said selective process allows furthermore to obtain the triazine compounds of formula (I) with a yield higher than about 90%.

As said, the additives of the present invention do not contain phosphor, are obtainable with a defined chemical structure in high yields by a simple and highly selective process. Said additives allow furthermore to broaden the application field of the perfluoropolyether lubricants in thermooxidative environment in the presence of metals, in particular at temperatures higher than 280° C., in combination with anti-rust properties and high shelf life at 25° C.

The lubricating compositions comprising the additives of the present invention can be used in the presence of metals and in oxidative environment (in the presence of air and oxygen) at high temperatures, higher than 200° C., without any substantial lubricant degradation phenomenon. In particular the lubricating compositions containing the additives of the present invention can be used even at temperatures of about 300° C.

Besides, as said, the compositions of the present invention have the advantage to be stable to storage at room temperature for long periods of time, thus overcoming the prior art drawbacks.

The Applicant has surprisingly and unexpectedly found that the compounds of the present invention, although containing non fluorinated substituents as the phenol groups, are dispersible in fluorinated oils at room temperature and do not show any substantial phase separation, thus allowing stability to storage (i.e. high shelf life).

As said, the additives of the present invention can be used in lubricating oils and greases. In particular the preferred greases are the fluorinated ones, more preferably perfluoropolyether base greases. In the case of perlfuoropolyether-based lubricating greases, the compositions contain, besides the additive of the present invention and the perfluoropolyether oil belonging to one or more of the above mentioned classes, as ah essential component, a thickener, in the amounts used in the prior art, as for example PTFE, sodium terephthalamate, calcium or lithium soaps, polyurea. Besides, said compositions can also contain other additives commonly used in grease technology, as talc, inorganic fillers, anti-wear additives. In the case of PTFE used as a thickener, the polymer primary particle sites, measured by electronic scanning microscopy (SEM), are between 0.02 and 0.25 micron. Said particles can be obtained, for example, by known microemulsion, emulsion, suspension polymerization processes.

The present invention will be better illustrated by the following Examples, which have a merely illustrative and not limitative purpose of the invention.

EXAMPLES

Characterization

Microoxidation Test

The microoxidation test reported in the Examples has been carried out by using the equipment described in the following publication: Carl E. Snyder, Jr. and Ronald E. Dolle, Jr., *ASLE Transactions*, 13(3), 171-180 (1975). The used operating conditions were the following:

Test temperature: 300° C.

Air flow: 11/h

Metals dipped in the fluid: stainless steel (AISI 304) and Ti alloy (Al 6%, V 4%)

Test duration: 24, 48, 72 hours

The lubricating composition to be tested is introduced in the glass test tube of the equipment shown in the reference FIG. 1, and the whole is weighed and brought to the test temperature. When 24, 48 or 72 hours have elapsed, depending on the test kind, the glass test tube, cooled at room temperture, is weighed again. The difference of weight before and after the heating determines the per cent weight loss of the composition under examination.

After the test the surface aspect of the metals which have been dipped in the tested composition is visually evaluated.

Test in Fog Chamber (Anti-rust)

A series of carbon steel (C15) (UNI) sheets having 50×100×2 mm sizes are prepared by polishing with abrasive papers (400-800 mesh) followed by cleaning and degreasing with a cloth soaked in n-hexane, and then dried. These sheets are treated by dip-coating in the test dispersion and then placed in the fog chamber. The fog chamber is formed of one sprayer, connected to a water reserve, which, by compressed air (P=3 atm) is capable to saturate with moisture the chamber at the temperature of 35° C. The sheets are left in the chamber closed and saturated with moisture and are controlled at time regular intervals by visual inspection up to the appearance of stains on the surface. The test evaluation is expressed according to the following classification:

(0) no rust stain;
(1) one/three corrosion spots having a diameter lower than 1 mm;
(2) three stains having a diameter higher than 1 mm or more stains having a diameter lower than 1 mm for a total of corroded surface lower than 1%;
(3) four or five stains having a diameter higher than 1 mm or more stains having a diameter lower than 1 mm for a total of corroded surface between 1% and 5%;
(4) corroded surface between 5% and 10%;
(5) corroded surface higher than 10%.

Kinematic Viscosity of the Perfluoropolyether Oil

The kinematic viscosity has been measured by capillary viscometer Cannon-Fenske according to the ASTM D445 method.

Preparation of the Additives

Example 1

Preparation of the additive (I) of formula:

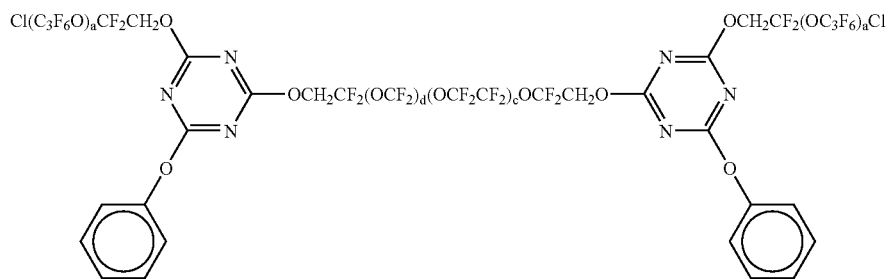

wherein c and d are integers such that c/d=2 and $OCH_2CF_2(OCF_2)_d(OCF_2CF_2)_cOCF_2CH_2O$ has an average molecular weight of 1,464

300 g of hexafluoroxylene, 12.7 g (0.068 moles) of 2,4,6-trichlorotriazine and 9 g (0.074 moles) of collidine are introduced in a 1 litre glass flask, equipped with mechanical stirring, thermometer and dripper. The reaction mixture is cooled to 0° C. and then 50 g (0.034 moles, 0,068 eq) of $HOCH_2CF_2(OCF_2)_d(OCF_2CF_2)_cOCF_2CH_2OH$ (MW=1,466) are slowly dripped, under stirring, maintaining the temperature inside the flask between 0° C. and 10° C.

When the alcohol dripping is over, the reaction mixture is kept under these conditions for about 2 hours, then it is brought to room temperature and left under these conditions for further 2 hours.

9 g (0.074 moles) of collidine are then added and the temperature brought to 30° C. Under these conditions 42.8 g (0.068 eq) of $Cl(C_3F_6O)_aCF_2OH$ (MW=631) are added by dripping under stirring. When the addition is over, the reaction is allowed to continue for about 4 hours under stirring. Additional 9 g (0.074 moles) of collidine and 6.4 g (0.068 eq) of phenol are then added to the reaction mixture. After the addition, the temperature is brought to 80° C. and the reaction is allowed to continue for about 6 hours.

After cooling, the precipitated collidine hydrochloride is then removed from the reaction mixture by filtration.

The liquid organic mass is then washed with 150 g of an aqueous HCl solution at 2% by weight. After separation of the organic phase the solvent is distilled and the product stripped at 130° C./1 mmHg for about 4 hours. 96.3 g of product with a yield equal to 92% are thus obtained.

The IR and NMR analyses ($^1H$, $^{13}C$ and $^{19}F$) confirm the structure and thus the high selectivity of the synthesis.

Example 2

Preparation of the additive (I) of formula:

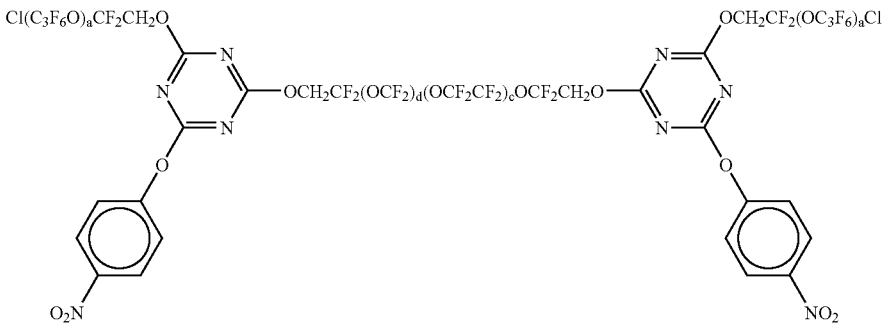

wherein c and d are integers such that c/d=2 and $OCH_2CF_2(OCF_2)_d(OCF_2CF_2)_cOCF_2CH_2O$ has an average molecular weight of 1,464.

The Example 1 was repeated but by using 9.4 g (0.068 eq) of p-nitrophenol instead of phenol.

97.8 g of product with a yield equal to 91% are thus obtained. The IR and NMR analyses ($^1H$, $^{13}C$ and $^{19}F$) confirm the structure and thus the high selectivity of the synthesis.

Example 3

Preparation of the additive of formula:

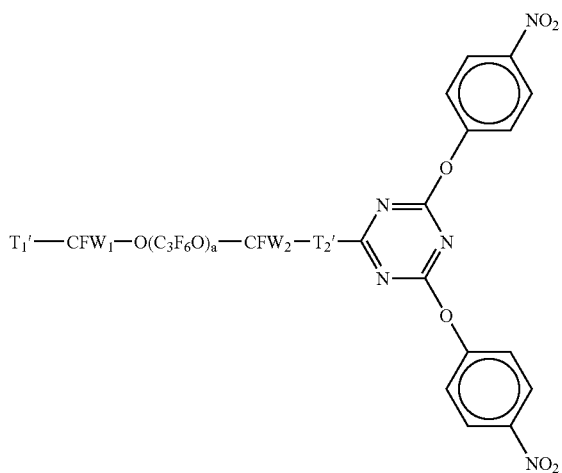

wherein a is an integer such that $T_1'$-$CFW_1$—$O(C_3F_6O)_a$—$CFW_2$-$T_2'$ has a number average molecular weight equal to 3770; $W_1$ and $W_2$ are equal to F or $CF_3$; T1' is equal to —F, —$CF_3$, —$C_2F_5$; $T_2'$ is equal to a 60/40 mixture of —$CH(CF_3)$O— and —$CH_2$—O—.

300 g of hexafluoroxylene, 6.35 g (0.034 moles) of 2,4,6-trichlorotriazine and 4.5 g (0.036 moles) of collidine are introduced in a 1 litre glass flask, equipped with mechanical stirring, thermometer and dripper. The reaction mixture is cooled to 0° C. and then 128 g (0.034 moles) of the compound (II) $T_1'$-$CFW_1$—$O(C_3F_6O)_a$—$CFW_2$-$T_2'$-H (MW=3,771), prepared according to the teaching of U.S. Pat. No. 5,124,058 herein incorporated by reference, are slowly dripped, under stirring, maintaining the temperature inside the flask between 0° C. and 10° C.

When the alcohol dripping is over, the reaction mixture is kept under these conditions for about 2 hours, then it is brought to room temperture and left under these conditions for further 2 hours.

9 g (0.074 moles) of collidine and 9.4 g (0.068 eq) of p-nitrophenol are then added. After the addition, the temperature is brought to 80° C. and the reaction is allowed to continue for about 6 hours.

After cooling, the precipitated collidine hydrochloride is then removed from the reaction mxiture by filtration.

The liquid organic mass is then washed with 150 g of an aqueous HCl solution at 2% by weight. After separation of the organic phase the solvent is distilled and the product stripped at 130° C./1 mmHg for about 4 hours. 133 g of product with a yield equal to 95% are thus obtained. The IR and NMR analyses ($^1H$, $^{13}C$ and $^{19}F$) confirm the structure and thus the high selectivity of the synthesis.

Example 4

Preparation of the additive of formula:

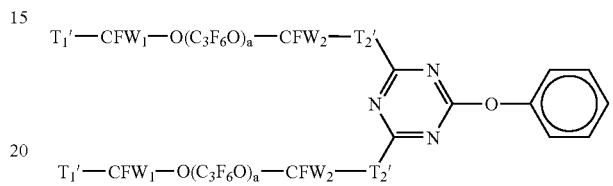

wherein a is an integer such that $T_1'$-$CFW_1$—$O(C_3F_6O)_a$—$CFW_2$-$T_2'$ has a number average molecular weight equal to 1295; $W_1$ and $W_2$ are equal to F or $CF_3$; T1' is equal to —F, —$CF_3$, —$C_2F_5$; $T_2'$ is equal to a 60/40 mixture of —CH$(CF_3)$C and —$CH_2$—O.

300 g of hexafluoroxylene, 7.1 g (0.038 moles) of 2,4,6-trichlorotriazine and 5 g (0.041 moles) of collidine are introduced in a 1 litre glass flask, equipped with mechanical stirring, thermometer and dripper.

The reaction mixture is cooled to 0° C. and then 50 g (0.038 moles) of the compound (II) $T_1'$-$CFW_1$—$O(C_3F_6O)_a$—$CFW_2$-$T_2'$-H (MW=1,296), prepared according to the teaching of U.S. Pat. No. 5,124,058 herein incorporated by reference, are slowly dripped under stirring, maintaining the temperature inside the flask between 0° C. and 10° C.

When the alcohol dripping is over, the reaction mixture is kept under these conditions for about 2 hours, then it is brought to room temperature and left under these conditions for further 2 hours.

5 g (0.041 moles) of collidine are then added and the temperature is brought to 30° C. Under these conditions, by dripping under stirring, additional 50 g (0.038 eq) of $T_1'$-$CFW_1$—$O(C_3F_6O)_a$—$CFW_2$-$T_2'$-H are added. When the addition is over, the reaction is allowed to continue for about 4 hours. Additional 5 g (0.041 moles of collidine and 3.6 g (0.088 eq) of phenol are then added to the reaction mixture. After the addition, the temperature is brought to 80° C. and the reaction is allowed to continue for about 6 hours.

After cooling, the precipitated collidine hydrochloride is then removed from the reaction mixture by filtration.

The liquid organic mass is then washed with 150 g of an aqueous HCl solution at 2% by weight. After separation of the organic phase the solvent is distilled and the product stripped at 130° C./1 mmHg for about 4 hours. 98.2 g of product with a yield equal to 92% are thus obtained. The IR and NMR analyses ($^1H$, $^{13}C$ and $^{19}F$) confirm the structure and thus the high selectivity of the synthesis.

Example 5 (Comparative)

Preparation of a triazine additive

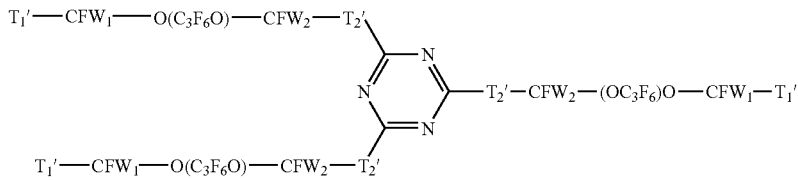

not containing aryl substituents, wherein a is an integer such that $T_1'$-$CFW_1$—$O(C_3F_6O)_a$—$CFW_2$-$T_2'$ has a number average molecular weight equal to 3770; $W_1$ and $W_2$ are equal to F or $CF_3$; $T_1'$ is equal to —F, —$CF_3$, —$C_2F_5$; $T_2'$ is equal to a 60/40 mixture of —CH($CF_3$)O— and —$CH_2$—O—.

300 g of hexafluoroxylene, 6.35 g (0.034 moles) of 2,4,6-trichlorotriazine and 13.5 g (0.108 moles) of collidine are introduced in a 1 litre glass flask, equipped with mechanical stirring, thermometer and dripper.

The reaction mixture is cooled to 0° C. and then 384 g (0.102 moles) of the compound (II) $T_1'$-$CFW_1$—$O(C_3F_6O)_a$—$CFW_2$-$T_2'$-H (MW=3,771) are slowly dripped, under stirring, maintaining the temperature inside the flask between 0° C. and 10° C.

When the alcohol dripping is over, the reaction mixture temperature is slowly brought to 80° C. and the reaction is allowed to continue for about 6 hours.

After cooling, the precipitated collidine hydrochloride is then removed from the reaction mixture by filtration.

The liquid organic mass is then washed with 150 g of an aqueous HCl solution at 2% by weight. After separation of the organic phase the solvent is distilled and the product stripped at 130° C./1 mmHg for about 4 hours. 370 g of product with a yield equal to 93% are thus obtained. The IR and NMR analyses ($^1H$, $^{13}C$ and $^{19}F$) confirm the structure and thus the high selectivity of the synthesis.

Application Tests

Example 6

50 g of a perfluoropolyether oil of the class (5), having kinematic viscosity at 20° C. of 260 cSt, commercially known as Fomblin® Z25, are added with 0.5 g of the additive of the Example 4 and then introduced in the glass test tube for the microoxidation test, in the presence of metals. After 24 hours at 300° C. under the indicated operating conditions, a weight loss of 1.1% was determined.

The metals dipped in the fluid during the test (stainless steel and Ti, Al, V alloy) did not show oxidation/attack signs, but resulted comparable with those not exposed to the treatment.

During the test the composition kept limpid and no development of smokes was observed.

Furthermore the composition obtained by adding the perfluoropolyether oil with the additive of the Example 4 has resulted stable at room temperature and it does not visually show any separation after 168 hours.

Example 7

The Example 6 was repeated but increasing the time of the microoxidation test to 48 hours. At the end of the test a loss of 1.46% by weight was measured.

Example 8

The Example 6 was repeated by using 0.5 g of the additive of the Example 1. After 24 hours at 300° C. under the indicated operating conditions a weight loss of 0.98% was measured. The metals dipped into the fluid during the test (stainless steel and Ti, Al, V alloy) do not show oxidation/attack signs, but are comparable with those not exposed to the treatment.

The composition obtained by adding the perfluoropolyether oil with the additive of the Example 1 resulted stable at room temperature and it did not visually show any phase separation after 168 hours.

Example 9

The Example 8 was repeated but increasing the time of the microoxidation test to 48 hours. At the end of the test a loss of 1.6% by weight was measured.

Example 10

The Example 8 was repeated but increasing the time of the microoxidation test to 72 hours. At the end of the test a loss of 2.2% by weight was measured.

Example 11

The Example 6 was repeated by using 0.5 g of the additive of the Example 3. After 24 hours at 300° C. under the indicated operating conditions a weight loss of 0.47% was measured. The metals dipped into the fluid during the test (stainless steel and Ti, Al, V alloy) do not show oxidation/attack sings, but are comparable with those not exposed to the treatment.

The composition obtained by adding the perfluoropolyether oil with the additive of the Example 3 resulted stable at room temperature and it did not visually show any separation after 168 hours.

Example 12

The Example 6 was repeated by using 0.5 g of the additive of the Example 2. After 24 hours at 300° C. under the indicated operating conditions a weight loss of 0.82% was measured. The metals dipped into the fluid during the test (stainless steel and Ti, Al, V alloy) do not show oxidation/attack signs, but are comparable with those not exposed to the treatment.

The composition obtained by adding the perfluoropolyether oil with the additive of the Example 2 resulted stable at room temperture and it did not visually show any separation after 168 hours.

Example 13 (Comparative)

The Example 6 was repeated in the absence of stabilizing additives. During the test a development of white smokes was observed. After 24 hours at 300° C. under the indicated operating conditions the oil was completely decomposed.

The metals dipped into the oil during the test (stainless steel and Ti, Al, V alloy) show evident oxidation/attack signs and a remarkable darkening of the surface.

Example 14 (Comparative)

The Example 6 was repeated but by using as stabilizing agent 0.5 g of a non triazine stabilizing additive of formula

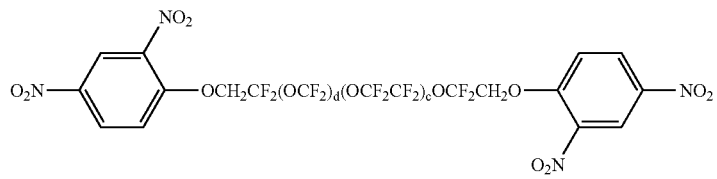

wherein the number average molecular weight of the chain is 1966 and c/d=1.2, prepared according to the Example 1 of EP 1,354,932.

After 24 hours at 300° C. under the indicated operating conditions a weight loss of 1.06% was measured. The metals dipped into the fluid during the test (stainless steel and Ti, Al, V alloy) did not show oxidation/attack signs, but were comparable with those not exposed to the treatment.

However the composition obtained by adding the perfluoropolyether oil with the additive having aryl end groups of EP 1,354,932 and not containing triazine rings shows evident phase separation at room temperature already within 24 hours.

Example 15 (Comparative)

The Example 6 was repeated but by using as stabilizing agent 0.5 g of the compound of the Example 5 (comparative).

After 24 hours at 300° C. under the indicated operating conditions, a weight loss of 49% was measured.

By comparing these data with those of stability of the Examples according to the invention, it results that the compounds containing triazine rings not substituted with aryl groups are not sufficient to guarantee a good stabilizing activity for perfluoropolyether oils in oxidative environment in the presence of metals at high temperatures.

Example 16

A lubricating composition is prepared containing 0,5 g of the additive of the Example 2, 9.5 g of a perfluoropolyether lubricant of structure (1), having kinematic viscosity at 20° C. of 40 cSt, commercially known as Fomblin® Y04. Said composition is then diluted with 190 g of a fluorinated solvent commercially known as Galden® SV90.

Then a metal sheet, cleaned according to what reported for the fog chamber test, is treated by dipping for 1 minute in said mixture. Said time elapsed, the sheet is taken and allowed to dry in a ventilated stove for 30 minutes at 60° C. to remove the solvent. Then the sheet is placed in the fog chamber for the test.

After 118 hours under the test conditions the sheet does not show corrosion signs.

Example 17 (Comparative)

The Example 16 was repeated without adding the invention additive and by using a lubricating mixture formed of 10 g of Fomblin® Y04 oil and 190 g of fluorinated solvent Galden® SV90.

After 118 h under the test conditions the sheet shows an extended corrosion between 5% and 10% of the total surface.

Example 18

The Example 16 was repeated without using the perfluoropolyether oil and by using a mixture formed of 0.5 g of the additive of the Example 2 and 199.5 g of fluorinated solvent Galden® SV90.

After 118 ore under the test conditions the sheet does not show corrosion signs.

Example 19 (Comparative)

The Example 16 was repeated by using only 200 g of fluorinated solvent Galden® SV90 (control test).

After 118 hours under the test conditions the sheet shows an extended corrosion higher than 10% of the total surface.

TABLE 1

Microoxidation test

| Ex. | Oil | Additive | Additive Conc. (% w/w oil) | Dispersion Aspect (at room T) | Duration test | Loss (% w/w) |
|---|---|---|---|---|---|---|
| 6 | Fomblin Z 25 | Ex. 4 | 1% | Homogeneous after 168 h | 24 h | 1.1 |
| 7 | Fomblin Z 25 | " | " | Homogeneous after 168 h | 48 h | 1.46 |
| 8 | Fomblin Z 25 | Ex. 1 | " | Homogeneous after 168 h | 24 h | 0.98 |
| 9 | Fomblin Z 25 | " | " | Homogeneous after 168 h | 48 h | 1.6 |
| 10 | Fomblin Z 25 | " | " | Homogeneous after 168 h | 72 h | 2.2 |
| 11 | Fomblin Z 25 | Ex. 3 | " | Homogeneous after 168 h | 24 h | 0.47 |
| 12 | Fomblin Z 25 | Ex. 2 | " | Homogeneous after 168 h | 24 h | 0.82 |
| 13 comp | Fomblin Z 25 | — | — | — | 24 h | Decomposed |
| 14 comp | Fomblin Z 25 | EP 1354932 | 1% | Phase Separation after 24 h | 24 h | 1.06 |
| 15 comp | Fomblin Z 25 | Triaz. without aryls | | | 24 h | 49 |

TABLE 2

Resistance test to corrosion (fog chamber)

| Ex. | Oil | Solvent | Additive | Concentration (% w/w of oil) | Corrosion |
|---|---|---|---|---|---|
| 16 | Fomblin Y04 | Galden SV 90 | Ex. 2 | 5 | NO |
| 17 comp | Fomblin Y04 | Galden SV 90 | — | — | 5-10% |
| 18 | — | Galden SV 90 | Ex. 2 | — | NO |
| 19 comp | — | Galden SV 90 | — | — | >10% |

The invention claimed is:

1. A perfluoropolyether compound of formula:

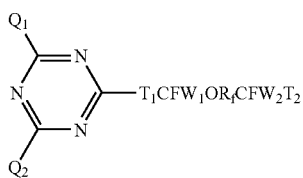
(I)

wherein

R$_f$ is a (per) fluoropolyoxyalkylene chain formed of one or more repeating units, statistically placed along the chain, having the following structure: (CFXO), (CF$_2$CF$_2$O), (CF$_2$CF$_2$CF$_2$O), (CF$_2$CF$_2$CF$_2$CF$_2$O), (CR$_6$R$_7$CF$_2$CF$_2$O), (CF(CF$_3$)CF$_2$O), (CF$_2$CF(CF$_3$)O), wherein X=F, CF$_3$; R$_6$ and R$_7$, equal to or different from each other, are selected from H, Cl, or perfluoroalkyl from 1 to 4 carbon atoms, said Rf having a number average molecular weight in the range 500-10,000;

W$_1$, W$_2$, equal to or different from each other, are —F or —CF$_3$;

T$_1$ is equal to —CHA$_a$—B$_a$ (CH$_2$CH$_2$O)$_{na}$— wherein A$_a$=H, CF$_3$;

B$_a$=O, S, NH; na is an integer from 0 to 6, extremes included;

T$_2$ is equal to —F, —CF$_3$, —C$_2$F$_5$, —(C$_2$F$_4$)Cl, or a group of formula:

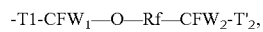

Q$_1$, Q$_2$, equal to or different from each other, are a perfluoropolyoxyalkylene chain of formula:

-T1-CFW$_1$—O—Rf—CFW$_2$-T'$_2$, wherein T'$_2$ is equal to —F, —CF$_3$, —C$_2$F$_5$, (C$_2$F$_4$)Cl; T$_1$, W$_1$ and W$_2$ have the above meaning; or a group of formula:

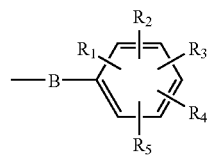

wherein B is equal to O, S, NH; R$_1$, R$_2$, R$_3$, R$_4$, R$_5$, equal to or different from each other, are selected from H, F, NO$_2$, CN, linear or branched $C_1$-$C_8$ perfluoroalkyl, carboxyl, phenyl (Ph), O-Ph, NH-Ph, S-Ph;

with the proviso that at least one of $Q_1$ and $Q_2$ is equal to:

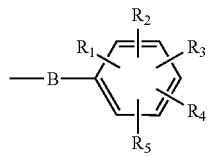

2. The compound according to claim 1, wherein the perfluoropolyether chain $R_f$ is selected from the following structures:

(A) —(CF$_2$CF(CF$_3$)O)$_a$(CFXO)$_b$— or
—(CF$_2$CF(CF$_3$)O)$_a$(CFXO)$_b$—CF$_2$(R'$_f$)CF$_2$—O—(CF$_2$CF(CF$_3$)O)$_a$(CFXO)$_b$ wherein R'f is a fluoroalkylene group from 1 to 4 C atoms; X is F or CF$_3$; a and b are integers such that the number average molecular weight is within the above range; a/b is between 10 and 100, b being different from 0;

(B) (CF$_2$CF$_2$O)$_c$ (CF$_2$O)$_d$(CF$_2$(CF$_2$)$_z$O)$_h$— wherein c, d and h are integers such that the number average molecular weight is within the above range; c/d, d being different from 0, is between 0.1 and 10; h/(c+d), (c+d) being different from 0, is between 0 and 0.05; z is 2 or 3; h can also be equal to 0;

(C) —(CF$_2$CF(CF$_3$)O)$_e$(CF$_2$CF$_2$O)$_f$(CFXO)$_g$— wherein X is F or CE$_3$; e, f, g are integers such that the number average molecular weight is in the above range; e/(f+g) is between 0.1 and 10, (f+g) being different from 0; f/g is between 2 and 10;

(D) (CF$_2$(CF$_2$)$_z$O)$_s$— wherein s is an integer such as to give the above molecular weight, z has the already defined meaning;

(E) —(CR$_6$R$_7$CF$_2$CF$_2$O)$_{j'}$— or
—(CR$_6$R$_7$CF$_2$CF$_2$O)$_{p'}$—R'$_f$—O—(CR$_6$R$_7$CF$_2$CF$_2$O)$_{q'}$— wherein R$_6$ and R$_7$ are equal to or different from each other and selected from H, Cl or perfluoroalkyl from 1 to 4 C atoms; R'$_f$ is a fluoroalkylene group from 1 to 4 C atoms; j', p' and q' are integers such as to have a molecular weight as the above mentioned one;

(F) —(CF(CF$_3$)CF$_2$O)j"— j" being an integer such as to give the above molecular weight.

3. The compound according to claim 2, wherein the structures $R_f$ are (A) or (B).

4. A method for thermally stabilizing fluorinated oils and greases in thermooxidative conditions in the presence of metals comprising adding the compound of claim 1.

5. A method for conferring anti-rust properties to fluorinated oils and greases comprising adding the compound of claim 1.

6. A method for conferring anti-rust properties to fluorinated oils and greases comprising adding the compound of claim 4.

7. A composition comprising:
from 99.95 to 90% by weight of a perfluoropolyether oil or a PFPE based grease on perfluoropolyether oils;
from 0.05 to 10% by weight of at least one of the triazine compounds of formula (I) of claim 1.

8. The composition according to claim 7, wherein the perfluoropolyether oil is selected from the following classes:

(1) E-O—[CF$_2$CF(CF$_3$)O]$_{m'}$(CFXO)n'-E' wherein
X is equal to —F or —CF$_3$;
E and E', equal to or different from each other, are selected from —CF$_3$, —C$_2$F$_5$ or —C$_3$F$_7$;
m' and n' axe integers such that the m'/n' ratio is between 20 and 1,000, n' being different from 0, and the viscosity of the product at 20° C. is between 10 and 4,000 cSt; the units being statistically distributed along the backbone, (2) C$_3$F$_7$O—[CF(CF$_3$)CF$_2$O]$_{o'}$-D wherein
D is equal to —C$_2$F$_5$ or —C$_3$F$_7$;
o' is an integer such that the viscosity of the product is within the range indicated under (1), (3) {C$_3$F$_7$O—[CF(CF$_3$)CF$_2$O]$_{p'}$—CF(CF$_3$)—}$_2$ wherein
p' is an integer such that the viscosity of the product is within the range indicated under (1), (4) E-O—[CF$_2$CF(CF$_3$)O]$_{q'}$(C$_2$F$_4$O)$_{r'}$(CFX)$_{s'}$-E' wherein
X is equal to —F or —CF$_3$;
E and E', equal to or different from each other, are selected from —CE$_3$, —C$_2$F$_5$ or —C$_3$F$_7$;
q', r' and s' are integers, including 0, so that the viscosity of the product is in the range indicated under (1), (5) E-O—(C$_2$F$_4$O)t', (CF$_2$O)$_{u'}$-E' wherein
E and E', equal to or different from each other, are selected from —CF$_3$, —C$_2$F$_5$ or —C$_3$F$_7$;
t' and u' are integers such that the t'/u' ratio is between 0.1 and 5, u' being different from 0, and the viscosity of the product is in the above reported range under (1), (6) E-O—(CF$_2$CF$_2$CF$_2$O)$_{v'}$-E' wherein
E and E', equal to or different from each other, are selected from —CE$_3$, —C$_2$F$_5$ or —C$_3$F$_7$;
v' is a number such that the viscosity of the product is in the above reported range under (1), (7) D-O—(CF$_2$CF$_2$O)$_{z'}$-D' wherein
D and D', equal to or different from each other, are selected between —C$_2$F$_5$ or —C$_3$F$_7$;
z' is an integer such that the viscosity of the product is within the above reported range under (1), (8) E$_1$-O(CF$_2$O)$_n$(CF$_2$CF$_2$O)$_m$—(CF$_2$CF$_2$CF$_2$O)$_p$(CF$_2$CF$_2$CF$_2$CF0)$_q$-E$_2$ wherein
E$_1$ and E$_2$ are perfluoroalkyl end groups equal to or different from each other, having formula
—(CF$_2$)$_z$CF$_3$, wherein z is an integer from 0 to 3; n, m, p, q are integers such that the viscosity is as defined under (1), m/n is between 2 and 20, n being different from 0; the ratio (p+q)/(m+n+p+q) is between 0.05 and 0.2, (m+n+p+q) being different from 0; n/(m+n+q+p) ranges between 0.05 and 0.4, (m+n+p+q) being different from 0.

9. The composition according to claim 8, wherein the perfluoropolyether oils are those of the classes (1), (4), (5) and (8).

10. The composition according to claim 7 comprising additives commonly used in perfluoropolyether lubricant formulations.

11. A process for preparing a perfluoropolyether compound of formula (I) of claim 1 comprising the following stages:

STAGE A)

i) reaction of a perfluoropolyoxyalkylene derivative having formula $$T''_1—CFW_1—O-R_f-CFW_2T''_2 \quad (II)$$

wherein $R_f$, $W_1$ and $W_2$ have the above meaning;

$T''_1$ and $T''_2$ can be equal to or different from each other, having general formula equal to —$CHA_a$—$B_a$($CH_2CH_2O$)$_{na}$—H, wherein $A_a$32 H, $CF_3$; $B_a$=O, S, NH; na is an integer from 0 to 6, extremes included; or selected from F, $CF_3$, $C_2F_5$, ($C_2F_4$) Cl, with the proviso that at least one of the two end groups $T''_1$ and $T''_2$ is equal to —$CHA_a$—$B_a$($CH_2CH_2O$)$_{na}$—H;

with a trihalo-triazine of formula:

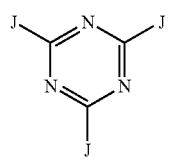
(III)

wherein J is selected from the group consisting of Cl and F;

at a temperature between 0° and 10° C., wherein the ratio between the equivalents of the compound (II) and the moles of (III) is equal to 1:1, in the presence of a solvent inert under the reaction conditions, capable to solubilize the reactants, and in the presence of an organic or inorganic base;

ii) reaction of the product obtained in i) with an equivalent of a derivative of formula:

$$Q\text{-}H \quad (IV)'$$

wherein Q has the above reported meaning for $Q_1$ and $Q_2$;

at a temperature in the range 25°-35° C.;

iii) reaction of the product obtained in ii) with an equivalent of a compound of formula (IV), equal to or different from the one used in step ii), at a temperature in the range 65° C.-100° C.;

STAGE B)

separation of the organic phase of the reaction mixture obtained in A) from the aqueous' phase and subsequent separation of the organic phase to remove the residual organic or inorganic insoluble salts;

STAGE C)

several washings of the liquid organic phase with acid water and subsequent separation of the obtained compound of formula (I) from the organic solvent.

12. A process according to claim 11, wherein in stage A) the inert solvent is selected from toluene, xylene, hexafluoroxylene, acetone, diethyl-ketone.

13. A process according to claim 11, wherein in stage A) the inorganic base is selected from NaOH, KOH, $Na_2CO_3$, $K2CO_3$; the organic base is selected from 2,6-dimethylpyridine, 2-methylquinoline, 2,4,6-trimethylpyridine (collidine).

14. A process according to claim 11, wherein the base is 2,4,6-trimethylpyridine.

15. A process according to claim 11, wherein the ratio between the equivalents of base and the sum of the equivalents of compounds (II) and (IV) used in the three steps of stage (A) is in the range 1:1-2:1.

16. Lubricating greases having a perfluoropolyether base comprising the additive of claim 1, a perfluoropolyether oil and a thickener selected from the group consisting of PTFE, sodium terephthalamate, calcium or lithium soaps, and polyurea.

17. Greases according to claim 16 comprising talc, inorganic fillers, anti-wear additives.

18. The lubricating composition of claim 7, wherein the perfluoropolyether oil or a PFPE based grease on perfluoropolyether oils has a concentration from 99.5 to 95% by weight.

19. The lubricating composition of claim 7, wherein the at least one of the triazine compounds of formula (I) has a concentration from 0.5 to 5% by weight.

20. A composition according to claim 10, wherein the additives are anti-wear additives.

* * * * *